United States Patent [19]

Pedersen et al.

[11] 4,200,584

[45] * Apr. 29, 1980

[54] MALEIC ANHYDRIDE PRODUCTION OVER MODIFIED PHOSPHOTUNGSTIC CATALYST

[75] Inventors: Svend E. Pedersen, Mentor, Ohio; Ming N. Sheng, Cherry Hill, N.J.

[73] Assignee: Atlantic Richfield Company, Los Angeles, Calif.

[*] Notice: The portion of the term of this patent subsequent to Mar. 6, 1996, has been disclaimed.

[21] Appl. No.: 966,550

[22] Filed: Dec. 5, 1978

Related U.S. Application Data

[63] Continuation-in-part of Ser. No. 853,970, Nov. 21, 1977, Pat. No. 4,143,056.

[51] Int. Cl.² ............................................ C07D 307/60
[52] U.S. Cl. ................................ 260/346.75; 252/437
[58] Field of Search ..................................... 260/346.75

[56] References Cited

PUBLICATIONS

Ai, Journal of Catalysis 49, pp. 313-319 (1977).

*Primary Examiner*—Henry R. Jiles
*Assistant Examiner*—Bernard Dentz
*Attorney, Agent, or Firm*—John R. Ewbank

[57] ABSTRACT

An unsaturated normal aliphatic hydrocarbon of 4 or 5 carbon atoms and an oxygen-containing gas react to form an effluent containing maleic anhydride as a result of a reaction in the presence of a catalyst consisting essentially of a mixture of the oxides of tungsten, phosphorus, a Group A metal, and a multivalent metal having an atomic number from 21 to 47, the sum of the oxides of the Group A metal and the multivalent metal constituting from 1% to 15% of the catalyst, the atom ratio of the Group A metal to the transition metal being within a range from about 1:1 to about 8:1 and the overall atomic ratios are such that W:P:A:M corresponds to 1:0.1–0.7:0.01–0.16:0.01–0.1. In preferred embodiments the reaction is conducted in the presence of from about 3% to about 50% by volume of steam, desirably from about 5% to about 7% by volume steam, whereby catalyst stability and selectivity are enhanced.

18 Claims, No Drawings

MALEIC ANHYDRIDE PRODUCTION OVER MODIFIED PHOSPHOTUNGSTIC CATALYST

RELATED APPLICATIONS

This application is a continuation in part of co-pending Sheng et al Ser. No. 853,970 filed Nov. 21, 1977, now U.S. Pat. No. 4,143,056, concerned with a thallium vanadium modified phosphotungstic catalyst for making maleic anhydride, all the disclosure of which is deemed here reiterated. The terminal portion of the life of this case is disclaimed so that it expires simultaneously with said U.S. Pat. No. 4,143,056.

BACKGROUND OF THE INVENTION

1. Field of the Invention

This invention relates to preparation of an effluent gas stream containing maleic anhydride as a result of oxidizing an organic material having at least 4 carbon atoms, and known to be a precursor for maleic anhydride in the presence of a catalyst functioning as a partial exidation catalyst at conditions favoring formation and preservation of maleic anhydride.

2. PRIOR ART

The preparation of maleic anhydride from normal butene is described in a series of Ueeda U.S. Pat. Nos. 3,906,008, 3,975,407, and 4,003,920 all the disclosures of which are deemed here reiterated. M. Ai has described "The Activity of $WO_3$ Based Mixed Oxide Catalysts", in the Journal of Catalysis, Volume 49, pages 305–312, and Volume 49, pages 313–319 (1977). A significant variety of methods for making maleic anhydride have been operated commercially for at least a while during recent decades. Benzene has continued to be a preferred feed stock but the oxidation of butene over a vanadium phosphate type of catalyst has been chosen for some recent plants.

Notwithstanding the persistent efforts by many researchers the search for an appropriate catalyst for manufacturing maleic anhydride has not ended.

SUMMARY OF THE INVENTION

In accordance with the present invention, an effluent stream containing maleic anhydride is prepared by a method using a feed gas stream comprising a major amount of carrier gas, a controlled amount of oxygen, and a controlled amount of an unsaturated aliphatic normal hydrocarbon containing 4 or 5 carbon atoms, the proportions of oxygen and hydrocarbon providing in said feed gas stream a non-explosive mixture at reaction conditions, and said feed gas stream is converted at a temperature from 250° C. to 650° C. in a catalytic zone employing a catalyst having as active ingredients the oxides of tungsten, phosphorus, a Group A metal and a multivalent metal, said catalyst being a phosphotungstic catalyst modified by minor amounts of a Group A metal oxide and the oxide of a multivalent metal having an atomic number from 21 to 47, the sum of the oxides of the Group A metal and the multivalent metal constituting from 1% to 15% of the catalyst, the atom ratio of A:M being within the range from about 1:1 to about 8:1, and the overall atomic ratios are such that W:P:A:M correspond to 1:0.1–0.7:0.01–0.16:0.01–0.1.

The nature of the invention is further clarified by reference to a plurality of examples.

EXAMPLES

Apparatus was prepared for making a comparative study of catalysts for the preparation of maleic anhydride by the oxidation of a dilute stream of normal butene. The apparatus was designed to permit automatic recording of much of the analytical data so that it was feasible to conduct a run over a prolonged period of time with minimized manpower for operation of laboratory facility for producing maleic anhydride. The effort was to obtain the data whereby various catalysts could be compared for selecting those catalysts having an attractive combination of stability, selectivity and activity.

Steam is formed during the oxidation of butene to maleic anhydride. Such steam is a poison to some catalysts. Other catalysts appear to be more satisfactory when a controlled amount of steam is employed as a carrier gas and/or accelerator in the reaction mixture.

The reactor was maintained at a uniform temperature by use of the fluidized bed. The temperature of the catalyst was monitored but the relatively minor fluctuations of the temperature are ignored in the reported data, which concentrate on the nominal temperatures.

The reactor was a stainless steel tube having an inside diameter of about ⅜ inch, and shaped as a "U" tube for holding the catalyst particles and the inert particles in the zones just before and subsequent to such catalyst bed. The catalyst granules were generally of the 8–14 mesh size. The reactive stream was sent downwardly through the catalyst zone and upwardly into the other arm of the "U" tube. The effluent from the maleic anhydride production was subjected to automatic recording measurements for gas chromotography.

In many of the preparations, about 50 ml of catalyst was positioned in the "U" tube through which passed a reactive stream consisting of about 1% by volume 1-butene at an apparent contact time of about 2.4 seconds. The maleic anhydride was caught in a water trap, and thus converted to maleic acid.

The preparation of maleic anhydride was conducted in a similar manner in a variety of controlled preparations and in a variety of examples. The difference between runs concern particularly the choice of catalyst.

Several catalysts were prepared which contain oxides of tungsten. It is convenient to describe the preparation of the oxides of tungsten by the calcination of a tungsten containing precursor such as ammonium tungstate, tungstic acid or ammonium metatungstate. The calcination is conducted at a temperature of about 300° C. to prepare an oxide of tungsten. There was prepared an aqueous solution containing: (a) phosphoric; (b) appropriate compounds for introducing a Group A metal; and (c) appropriate compounds for introducing a transition metal having an atomic number from 21 to 47. The proportions of the Group A metal to the transition metal were carefully controlled so that in the final catalyst the ratio of A:M would be within the range from 1:1 to 8:1. A dispersion of 500 ml of catalyst precursors was prepared by adding 360 g of powder of said oxide of tungsten to the thus prepared aqueous solution. The bulk of the water was removed by heating to provide a homogenous paste which was thereafter dried to a solid in an oven maintained at 120° C. The dried solids were pulverized and activated by heating in air at 500° C. for two hours. The activated powder was subjected to mechanical pressure to form pellets and the pellets were crushed and sieved to retain particles in the 8-14 mesh size.

Each catalyst was analyzed and it was established that the atomic ratios or W:P:A:M were satisfactory. Thus the atom percent of transition metal was 12-100% of the atom percent of the Group A metal. The Group A to transition metal atom ratio was from about 1:1 to about 8:1.

The gaseous effluent from the reactor was subjected to automatically recording measurements by I.R. and gas chromatography for determining the concentration in the effluent stream of carbon dioxide, carbon monoxide, maleic anhydride and hydrocarbon. The reactant stream flowed through a series of water traps adapted to absorb all of the maleic anhydride and/or other normally solid and/or normally liquid compounds of the reactant stream. The maleic anhydride reacted with the aqueous solution in the traps to form maleic acid. The aqueous solution containing the maleic acid was analyzed for minor by-products.

In each preparation of maleic anhydride in Examples 1-21, the volume of catalyst was 50 ml, the reactant stream consisted of air containing 1% by volume 1-butene, at an apparent contact time of 2.4 seconds. The mass balance was calculated for each preparation and only runs in which such data confirmed the significant reliability of the analyses are reported. In those preparations featuring injection of steam, the initial measurement of steam injection rate was on the basis of volume percent of feed.

Data relating to the preparation of maleic anhydride in Examples 1-21 are shown in Tables I and II.

Exact comparisons amongst examples (and/or the larger number of preparations of MA deemed redundant and not reported herein) are not feasible because of variations in temperature, space rate, stability, steam content, etc., but the tabulated data provide useful guidance in recognizing significant factors affecting catalyst composition.

Table I

MA formation over Modified Phosphotungstic Catalyst

| Code | Catalyst W:P:A:M 1:0.238:A:M A | M | A/M | Contact sec | Temp °C. | g/hr $H_2O$ addn. | Conv. % | MA Select Mol % | Yield MA mol % | CO mol % | $CO_2$ mol % | Acetic Acid % | Acrylic Acid % |
|---|---|---|---|---|---|---|---|---|---|---|---|---|---|
| Con A | 0.02Tl | none | inf | 2.5 | 445 | none | 100 | 54.0 | 54.0 | 22.5 | 19.5 | 0.9 | 1.1 |
| Con B | none | 0.04Ti | 0 | 2.4 | 445 | none | 100 | 53.8 | 53.8 | 23.0 | 20.5 | 0.6 | 0.5 |
| Ex 1 | 0.04Tl | 0.04Ti | 1 | 2.4 | 445 | none | 100 | 57.6 | 57.6 | 23.0 | 16.5 | 0.9 | 1.5 |
| Ex 2 | 0.04Tl | 0.02Ti | 2 | 2.5 | 445 | none | 100 | 60.8 | 60.8 | 21.0 | 15.3 | 0.7 | 1.1 |
| Ex 3 | 0.08Tl | 0.02Ti | 4 | 2.4 | 460 | none | 87 | 64.1 | 55.7 | 18.3 | 13.5 | 0.5 | 1.3 |
| Ex 4 | 0.08Tl | 0.04Ti | 2 | 2.5 | 445 | none | 65 | 59.5 | 38.7 | 19.2 | 16.3 | 1.1 | 0.9 |
| Ex 5 | 0.08Tl | 0.08Ti | 1 | 2.4 | 445 | none | 77 | 58.2 | 44.8 | 19.3 | 15.1 | 0.9 | 1.9 |
| Ex 6 | 0.04In | 0.04Ti | 1 | 2.5 | 445 | none | 100 | 50.1 | 50.1 | 26.2 | 20.9 | 0.4 | 0.7 |
| Ex 7 | 0.04K | 0.02Ti | 2 | 2.5 | 445 | none | 100 | 55.2 | 55.2 | 20.6 | 19.6 | 1.4 | 2.1 |
| Ex 8 | 0.04K | 0.02Ti | 2 | 2.5 | 445 | 5 | 100 | 58.3 | 58.3 | 21.6 | 14.9 | 1.8 | 1.6 |
| Ex 9 | 0.04Ca | 0.02Ti | 2 | 2.4 | 445 | none | 100 | 55.7 | 55.7 | 21.8 | 19.2 | 0.2 | 1.1 |
| Ex 10 | 0.04Ca | 0.02Ti | 2 | 2.5 | 445 | 5 | NA | 58.1 | 58.1 | 20.1 | 17.1 | 2.5 | 1.6 |
| Ex 11 | 0.02Cs | 0.02Ti | 1 | 2.4 | 445 | none | 100 | 57.5 | 57.5 | 23.5 | 17.3 | 0.4 | 1.0 |
| Ex 12 | 0.04Cs | 0.02Ti | 2 | 2.4 | 445 | none | 100 | 58.1 | 58.1 | 21.6 | 15.7 | 0.5 | 1.9 |

TABLE II

MA FORMATION OVER MODIFIED PHOSPHOTUNGSTIC CATALYST

| Code | Catalyst W:P:A:M 1:0.238:A:M A | M | A/M | Contact sec | Temp °C. | Conv. % | MA Select Mol % | Yield MA mol % | CO mol % | $CO_2$ mol % | Acetic Acid % | Acrylic Acid % |
|---|---|---|---|---|---|---|---|---|---|---|---|---|
| Ex 13 | 0.12Tl | 0.08Ti | 1.5 | 2.4 | 460 | 85 | 59.7 | 50.8 | 21.2 | 16.4 | 0.5 | 2.0 |
| Ex 14 | 0.12Tl | 0.02Cr | 6 | 2.5 | 460 | 98 | 56.2 | 56.2 | 16.9 | 21.6 | 0.4 | 0.5 |
| Ex 15 | 0.12Tl | 0.02Mn | 6 | 2.4 | 460 | 97 | 57.8 | 57.8 | 19.9 | 16.0 | 0.5 | 1.1 |
| Ex 16 | 0.12Tl | 0.02Co | 6 | 3.0 | 500 | 98 | 55.8 | 55.8 | 19.7 | 18.1 | 0.6 | 1.4 |
| Ex 17 | 0.12Tl | 0.02Ni | 6 | 2.5 | 460 | 79 | 50.0 | 39.5 | 20.5 | 24.5 | 0.7 | 0.5 |
| Ex 18 | 0.12Tl | 0.02Fe | 6 | 2.4 | 460 | 72 | 47.6 | 34.3 | 14.7 | 32.4 | 0.6 | 0.9 |
| Ex 19 | 0.12Tl | 0.02Mo | 6 | 2.4 | 445 | 100 | 47.0 | 47.0 | 20.2 | 29.4 | 0.8 | 1.0 |
| Ex 20 | 0.12Tl | 0.02Zr | 6 | 2.4 | 460 | 100 | 61.0 | 61.0 | 18.0 | 15.1 | 0.9 | 0.7 |
| Ex 21 | 0.12Tl | 0.02Nb | 6 | 2.5 | 460 | 97 | 59.0 | 57.3 | 14.1 | 20.5 | 0.9 | 1.6 |

By the present invention it has been discovered that a phosphotungstic matrix is desirably promoted, not by a single metal oxide, but by the combination of a Group A metal oxide and a transition metal oxide having an atomic number from 21 to 47 with the unit atomic ratio of the Group A metal to transition metal being kept within the range from 1 to 8, i.e. from 1:1 to 8:1.

The invention claimed is:

1. In the method for the production of an effluent stream containing maleic anhydride, said method using a feed gas stream comprising a major amount of carrier gas, a controlled amount of oxygen, and a controlled amount of an unsaturated aliphatic normal hydrocarbon containing 4 or 5 carbon atoms, the proportions of oxygen and hydrocarbon providing in said feed gas stream a non-explosive mixture at reaction conditions, and said feed gas stream is converted at a temperature from 250° C. to 650° C. in a catalytic zone to form an effluent stream containing maleic anhydride, the improvement which consists of:

employing as the catalyst in said catalytic zone a catalyst having as active ingredients the oxides of tungsten, phosphorus, a Group A metal and a multivalent metal, said catalyst being a phosphotungstic catalyst modified by minor amounts of a Group A oxide and the oxide of a multivalent metal having an atomic number from 21 to 47, the sum of the oxides of the Group A metal and the multivalent metal (i.e. M) constituting from 1% to 15% by weight of the catalyst, the atom ratio of A:M being within the range from about 1:1 to about 8:1, and the overall atomic ratios are such that W:P:A:M correspond to 1:0.1–0.7:0.01–0.16:0.01–0.1.

2. The method of claim 1 in which the composition of the carrier gas is controlled to include from about 3 to about 50 volume percent steam.

3. The method of claim 1 in which the unsaturated aliphatic hydrocarbon is a gas stream containing a predominant volume of normal butenes.

4. The method of claim 1 in which the Group A oxide is potassium oxide.

5. The method of claim 1 in which the Group A oxide is calcium oxide.

6. The method of claim 1 in which the Group A oxide is cesium oxide.

7. The method of claim 1 in which the Group A oxide is indium oxide.

8. The method of claim 1 in which the Group A oxide is thallium oxide.

9. The method of claim 1 in which the multivalent metal oxide is titanium oxide.

10. The method of claim 1 in which the multivalent metal oxide is chromium oxide.

11. The method of claim 1 in which the multivalent metal oxide is manganese oxide.

12. The method of claim 1 in which the multivalent metal oxide is iron oxide.

13. The method of claim 1 in which the multivalent metal oxide is cobalt oxide.

14. The method of claim 1 in which the multivalent metal oxide is nickel oxide.

15. The method of claim 1 in which the multivalent metal oxide is copper oxide.

16. The method of claim 1 in which the multivalent metal oxide is zirconium oxide.

17. The method of claim 1 in which the multivalent metal oxide is molybdenum oxide.

18. The method of claim 1 in which the multivalent metal oxide is silver oxide.

* * * * *